United States Patent [19]

Elmore

[11] Patent Number: 4,749,742

[45] Date of Patent: Jun. 7, 1988

[54] SOLID PHASE PEPTIDE SYNTHESIS

[75] Inventor: Donald T. Elmore, Belfast, Ireland

[73] Assignee: The Queens's University of Belfast, Ireland

[21] Appl. No.: 888,029

[22] Filed: Jul. 18, 1986

[51] Int. Cl.$^4$ .................. C08L 89/00; C08F 283/00
[52] U.S. Cl. .................. 525/54.11; 530/334
[58] Field of Search .................. 525/54.1, 54.11; 530/333, 334, 338

[56] References Cited

U.S. PATENT DOCUMENTS

| 4,115,305 | 9/1978 | Hornby et al. | 525/54.2 |
| 4,515,920 | 5/1985 | Erickson | 525/54.11 |
| 4,569,967 | 2/1986 | Kornreich et al. | 525/54.11 |

Primary Examiner—Delbert R. Phillips
Assistant Examiner—Nathan M. Nutter
Attorney, Agent, or Firm—Harry M. Weiss

[57] ABSTRACT

A method of solid phase peptide synthesis and a reusable insoluble polymer resin having functional groups of the formula

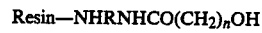

Resin—NHRNHCO(CH$_2$)$_n$OH wherein R is an branched or straight chain alkyl or cycloalkyl group having 2 to 20 carbon atoms, an aromatic group, substituted aromatic group, heterocyclic group or substituted heterocyclic group preferably 1,4-dimethylcyclohexane, and n is an integer, preferably 3. Phosphorylation followed by reaction with a diol, preferably 1,4-bis(hydroxymethyl)benzene, affords a substrate upon which peptides may be synthesized by repeated deprotection and coupling with protected amino acids.

22 Claims, No Drawings

SOLID PHASE PEPTIDE SYNTHESIS

BACKGROUND OF THE INVENTION

This invention relates generally, to a method of solid phase peptide synthesis and to materials, for use in performance of the method. More particularly, the present invention relates to a method of solid state peptide synthesis and a novel polymer resin having a diamine and lactone condensation product compound contained thereon for providing a protection/deprotection site for amino acid linkage and peptide formation.

While the use of insoluble polymer resins, such as polyamide, as substrates for peptide synthesis is well established, the currently available and commonly used resins are expensive and must be discarded after a single use. In contradistinction to these conventional resins, the present invention provides and employs a modified resin which may be enzyme treated to produce a reusable resin.

SUMMARY OF THE INVENTION

Accordingly, it is an object of the present invention to provide a method of solid phase peptide synthesis employing a polymer resin and a condensed diamine and lactone as a distancing group.

It is another object of the present invention to provide a polymer resin having a condensed diamine and lactone to provide a spacial distance between the resin and the reactive dialkylphosphate ester group for coupling to a protected amino acid upon which the peptide is formed.

DESCRIPTION OF THE PREFERRED EMBODIMENT

According to the preferred embodiment of the present invention, there is provided a method of solid phase peptide synthesis including the steps of:

combining an insoluble polymer resin with a diamine and a lactone; the diamine having the formula:

H$_2$NRNH$_2$ wherein R is selected from the group consisting of branched or straight chain alkyl or cycloalkyl compounds having 2 to 20 carbon atoms, aromatic, substituted aromatic, heterocyclic and substituted heterocyclic compound and the lactone having the formula:

CHX(CH$_2$)$_n$CHYCO.O wherein X and Y are each selected from the group consisting of hydrogen, an alkyl group having from 1 to 5 carbon atoms and NHZ where Z is selected from aroyl or other protecting groups and n is 0, 1, 2, or 3 to produce an alcohol of formula:

Resin—NHRNHCOCHY(CH$_2$)$_n$CHXOH phosphorylating the resulting resin alcohol compound with an arylphosphorodichloridate to produce an alkyl arylphosphorochloridate;
treating the alkyl arylphosphorochloridate with a compound of formula:

HO(CH$_2$)$_k$R$_1$(CH$_2$)$_m$OH wherein k and m are integers from 1 to 4, and R$_1$ is a cycloalkyl group, aromatic group, substituted aromatic group, heterocyclic group or substituted heterocyclic group to produce a phosphotriester;
treating the phosphotriester with base to produce a dialkylphosphate ester of the formula:

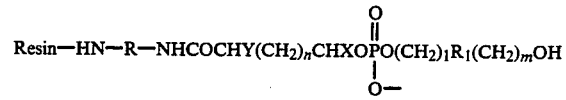
Resin—HN—R—NHCOCHY(CH$_2$)$_n$CHXOPO(CH$_2$)$_1$R$_1$(CH$_2$)$_m$OH condensing the dialkylphosphate ester with a protected amino acid anhydride;
forming a peptide by repeating a process of deprotection and coupling with protected amino acids,
treating the peptide with phosphodiesterase to cleave the peptide from the resin.

The free peptide may be obtained by removal of the diol group by catalytic hydrogenolysis, treatment with strong acid or by use of an appropriate enzyme.

The resin resultant from the treatment with phosphodiesterase may be treated with alkaline phosphatase to produce the alcohol which can be reused. The cleaved peptide derivative may also be treated with alkaline phosphatase to give a peptide ester. A peptide amide may be obtained by cleavage of the peptide from the resin with ammonia.

Initial treatment of the insoluble resin with the diamine compound serves to provide a spacial distance between the subsequently formed phosphate and the surface of the resin. Distancing the reactive phosphate group from the resin surface facilitates hydrolysis by phosphodiesterase which woud otherwise be conformationally inhibited. Preferred diamine compounds have a rigid carbon skeleton such as cycloaliphatic, heterocyclic, aromatic or other rings.

It has been found desirable, according to the preferred embodiment of the present invention, to condense the diamine and lactone to form an alcohol-amino compound of the formula:

H$_2$NRNHCOCHY(CH$_2$)$_n$CHXOH wherein R is selected from the group consisting of an alkyl or cycloalkyl group having 1 to 20 carbon atoms, an aromatic, substituted aromatic, heterocyclic and substituted heterocyclic compounds and n is 0, 1, 2 or 3.

This amino-alcohol compound may be conveniently condensed with the resin to produce the resin alcohol compound. Alternatively the diamine may first be condensed with the resin and the resin diamine condensation product being, in turn, condensed with the lactone to produce the resin alcohol compound. Combination of the resin and alcohol-amino compound is, however, preferred to minimize side reactions products thereby providing a cleaner reactive resin product having superior physical properties.

The preferable diamines are the 1,3- or 1,4-isomers of bis(aminomethyl-cyclohexane).

Preferred lactones have n=1 and one of X or Y being hydrogen the other being hydrogen or methyl.

Especially preferred lactones are γ-butyrolactone or a protected homoserine lactone, i.e. wherein n is 3, such as N-acetyl homoserine lactone.

4-Nitrophenylphosphorodichloridate has been found to be a suitable phosphorylating agent, however other compounds having labile leaving groups may be alternatively employed as phosphorylating agents.

A preferred diol is 1,4-bis(hydroxymethyl)benzene but other 4-substituted benzyl alcohols are also preferred. 1,3 bis(hydroxymethyl)benzene may also be used but is more expensive. An alternative reagent the isomers of bis(hydroxymethyl)furan.

Use of a polyacrylamide resin is preferred although other resins known to those skilled in the art, such as polystyrene, may be employed.

The protected amino acid anhydride is preferably the N-fluorenylmethoxycarbonyl (Fmoc) derivative, although the t-butyloxycarbonyl (Boc), O-tertiary butyl or 4-methoxy-2,3,6-trimethylbenzenesulphonyl (Mtr) derivatives may be used alternatively.

According to the further object of the present invention there is provided a solid phase peptide synthesis substrate comprising a functionalized insoluble polymer resin alcohol having the formula:

Resin—NHRNHCOCHY(CH$_2$)$_n$CHXOH wherein R is selected from the group consisting of branched or straight chain alkyl or cycloalkyl compounds having 2 to 20 carbon atoms, aromatic, substituted aromatic, heterocyclic and substituted heterocyclic compounds, X and Y are each selected from the group consisting of hydrogen, an alkyl group having from 1 to 5 carbon atoms and NHZ where Z is selected from aroyl or other protecting groups and n is 0, 1, 2 or 3.

The invention is further described, but not limited, with reference to the following example.

EXAMPLE

Preparation of 1-n-(4'-hydroxybutanoyl)amino-methyl-3-aminomethyl cyclohexane 1,3-bis(aminomethyl)cyclohexane (30 g 0.21 moles) and γ-butyrolactone (18 g 0.21 moles) were stirred together. After about 30 minutes, the flask became warm and after several hours, the mixture was extremely viscous. Dioxane (50 ml) was added and the mixture was heated to approximately 80° C. for 6 h with stirring. The bulk of the solvent was removed in a rotary evaporator the dioxane remainder and any unreacted diamine was removed at <1 mm pressure at 100° C. The product (45 g) was a viscous oil which was homogeneous on thin-layer chromatography and could be used without further purification.

Derivatization of polyacrylamide resin

A polyacrylamide resin with functional ester groups (e.g. "Pepsyn K", Cambridge Research Biochemicals, Cambridge, UK (2.0 g) was suspended in NN-dimethylformamide (50 ml) and 1-N-(4'-hydroxanoyl-)aminomethyl-3-aminomethyl-cyclohexane (10 g) was added. The resultant mixture was agitated at 30° C. for 4 days and the resin was washed 10 times with 20 ml aliquots of NN-dimethylformamide. A small portion of the product resin was tested for the absence of free amino groups by the ninhydrin reagent.

The foregoing resin derivative was treated with p-nitrophenyl phosphorodichloridate (5 g) in NN-dimethylformamide (25 ml) followed by pyridine (25 ml) and the mixture was agitated under nitrogen for 27 h during which time the supernatant turned from pale red to almost black in color. The supernatant was removed and the resin was washed by resuspension once with pyridine-NN-dimethylformamide (40 ml; 1:1 by volume) and five times with aliquots of NN-diamethylformamide (25 ml). The product resin turned a golden yellow color as a result of the phosphorylation step.

The product from the previous step was treated with a solution of 1,4-bis(hydroxymethyl)benzene in NN-dimethylformamide (20 ml and pyridine (20 ml)) with agitation for 40 h. The supernatant was removed and the product resin was washed by resuspension once with a pyridine-NN-dimethylformamide mixture (40 ml; 1:1 by volume) and five times with 25 ml aliquots of NN-dimethylformamide.

The product from the previous step was suspended for 3 h in a mixture of NN-dimethylformamide (20 ml), piperidine (20 ml) and water (20 ml) in order to hydrolyze the phosphotriester. The resultant resin was washed by resuspension twice in the pyridine-N,N-dimethylformamide mixture, twice with NN-dimethylformamide-piperidine (1:1 by volume), five times with NN-dimethylformamide, twice with NN-dimethylformamide-methanol (1:1 by volume), five times with methanol, twice with methanol-dichloromethane (1:1 by volume) and five times with dichloromethane. The derivatized resin was filtered and dried over P$_2$O$_5$ and silica gel in a desiccator.

Procedure for typical synthesis of peptides using a phosphate-type matrix

Coupling steps were generally carried out with symmetrical anhydrides of 9-fluorenylmethoxy carbonyl (Fmoc) protected amino acids in NN-dimethylformamide using a 2-6 fold excess of anhydride. Where required, functional side chains of Fmoc-amino acids were protected with appropriate group such as N-tert-butoxycarbonyl (Boc), O-tert-butyl, 4-methoxy-2,3,6-trimethylbenzenesulphonyl (Mtr). In the case of Fmoc-asparagine and Fmoc-glutamine, coupling was achieved using a reactive ester (e.g. p-nitrophenyl) in the presence of 1-hydroxybenzotriazole in NN-dimethylformamide. After completion of each coupling step, the Fmoc-protecting group was removed by exposure to piperidine in NN-dimethylformamide. Alternatively, the peptide could be assembled using Boc-amino acids.

After completion of the assembly of the peptide on the resin, all protecting groups could be removed by standard procedures or left intact for further coupling to other peptides by classical solution methods.

Procedures for detachment of peptides from a phosphate-type matrix

The peptide could be recovered as a O-terminal amide by treatment with methanol saturated with ammonia. The resin was reusable after washing with NN-dimethylformamide.

The peptide could be recovered as a C-terminal p-hydroxymethylbenzyl ester by a two-stage enzymatic cleavage process, as follows: The resin was first exposed to phosphodiesterase (e.g. from spleen) in 0.15M sodium acetate buffer (pH 5.0) containing 0.01M ethylenediamine tetraacetate. It was important to irreversibly inhibit any contaminating proteinases, for example, by prior treatment with iodoacetamide. The second cleavage step was achieved by exposure to alkaline phosphomoneasterase at pH 10. The recovered resin could be recycled by entering the derivatization process at the stage involving phosphorylation with p-nitrophenyl phosphorodichloridate. If recycling of the resin was not essential, only the first cleavage step with phosphodiesterase was necessary.

Irrespective of whether phosphodiesterase was used alone or followed by treatment with phosphomonesterase, the peptide with a free terminal carboxyl group could be obtained by cleavage of the substituted benzyl ester function using 33% HBr in acetic acid.

In all cases it was desirable to subject the isolated peptide to purification, for example, by high-performance liquid chromatography.

Using the above methodology, peptides such as Leu$^5$-enkephalin, casomorphine and substance P of high purity have been synthesized in good yield.

While the invention has been particularly shown and described in reference to the preferred embodiments thereof, it will be understood by those skilled in the art that changes in form, materials, details or compounds may be made therein without departing from the spirit and scope of the invention.

I claim:

1. A method of solid phase peptide synthesis, comprising the steps of:

combining an insoluble polymer resin, a diamine and a lactone; said diamine having the formula:

H$_2$NRNH$_2$ wherein R is selected from the group consisting of branched or straight chain alkyl or cycloalkyl compounds having 2 to 20 carbon atoms, aromatic, substituted aromatic, heterocyclic and substituted heterocyclic compounds, and said lactone having the formula:

$$\overline{\phantom{xx}CHX(CH_2)_nCHYCO.O\phantom{xx}}$$

wherein X and Y are each selected from the group consisting of hydrogen, branched or straight chain alkyl group having 1 to 5 carbon atoms and NHZ, wherein Z is selected from the group consisting of aryl, aroyl or other protecting group, and o is 0, 1, 2 or 3, to produce a resin alcohol having the formula:

Resin—NHRNHCOCHY(CH$_2$)$_n$CHXOH phosphorylating the resin alcohol with an arylphosphorodrichloridate to produce an alkyl arylphosphorochloridate;

treating the alkyl arylphosphorochloridate with a diol compound having the formula:

HO(CH$_2$)$_k$R$_1$(CH$_2$)$_m$OH wherein l and m are integers from k to 4, and R$_1$ is a cycloalkyl group, aromatic group, substituted aromatic group, heterocyclic group or substituted heterocyclic group to produce as phosphotriester;

treating the phosphotriester with a base to produce a dialkylphosphate ester of formula:

$$\text{Resin—HN—R—NHCOCHY(CH}_2)_n\text{CHXO}\overset{\overset{\text{O}}{\|}}{\underset{\text{O}^-}{\text{P}}}\text{O(CH}_2)_l\text{R}_1(\text{CH}_2)_m\text{OH}$$

condensing said dialkylphosphate ester with a protected amino acid anhydride;

forming a peptide by repeating a process of deprotection and coupling with protected amino acids, treating the peptide with phosphodiesterase to cleave the peptide from the resin.

2. The method of solid phase peptide synthesis according to claim 1, wherein said step of combining said diamine, said lactone and said resin, further comprises the steps of:

condensing said diamine with said lactone; and combining said diamine-lactone product with said insoluble polymer resin.

3. The method of solid phase peptide synthesis according to claim 1, wherein said diamine is selected from the group consisting of the 1,3- and 1,4-isomers of bis(aminomethyl)cyclohexane.

4. The method of solid phase peptide synthesis according to claim 2, wherein said diamine is selected from the group consisting of the 1,3- and 1,4-isomers of bis(aminomethyl)cyclohexane.

5. The method of solid phase peptide synthesis according to claim 1, wherein said lactone is γ-butyrolactone.

6. The method of solid phase peptide synthesis according to claim 2, wherein said lactone is γ-butyrolactone.

7. The method of solid phase peptide synthesis according to claim 3, wherein said lactone is γ-butyrolactone.

8. The method of solid phase peptide synthesis according to claim 1, wherein said lactone is a protected homoserine lactone.

9. The method of solid phase peptide synthesis according to claim 2, wherein said lactone is a protected homoserine lactone.

10. The method of solid phase peptide synthesis according to claim 3, wherein said lactone is a protected homoserine lactone.

11. The method of solid phase peptide synthesis according to claim 1, wherein said diol is 1,4-bis(hydroxymethyl)benzene.

12. The method of solid phase peptide synthesis according to claim 2, wherein said diol is 1,4-bis(hydroxymethyl)benzene.

13. The method of solid phase peptide synthesis according to claim 3, wherein said diol is 1,4-bis(hydroxymethyl)benzene.

14. The method of solid phase peptide synthesis according to claim 5, wherein said diol is 1,4-bis(hydroxymethyl)benzene.

15. The method of solid phase peptide synthesis according to claim 6, wherein said diol is 1,4-bis(hydroxymethyl)benzene.

16. The method of solid phase peptide synthesis according to claim 7, wherein said diol is 1,4-bis(hydroxymethyl)benzene.

17. The method of solid phase peptide synthesis according to claim 8, wherein said diol is 1,4-bis(hydroxymethyl)benzene.

18. The method of solid phase peptide synthesis according to claim 9, wherein said diol is 1,4-bis(hydroxymethyl)benzene.

19. The method of solid phase peptide synthesis according to claim 10, wherein said diol is 1,4-bis(hydroxymethyl)benzene.

20. The method of solid phase peptide synthesis according to claim 1, wherein said peptide is cleaved from the resin by treatment with phosphodiesterase and alkaline phosphatase.

21. The method of solid phase peptide synthesis according to claim 2, wherein said peptide is cleaved from the resin by treatment with phosphodiesterase and alkaline phosphatase.

22. A reusable solid phase peptide synthesis substrate, comprising an insoluble polymer resin having functional groups and having the formula:

Resin—NHRNHCOCHY(CH$_2$)$_n$CHXOH wherein R is selected from the group consisting of branched or straight chain alkyl or cycloalkyl compounds having 2 to 20 carbon atoms, aromatic, substituted aromatic, heterocyclic and substituted heterocyclic compounds, and wherein X and Y are each selected from the group consisting of hydrogen, branched or straight chain alkyl group having 1 to 5 carbon atoms and NHZ, wherein Z is selected from the group consisting of aryl, aroyl or other protecting group, and n is 0, 1, 2 or 3.

* * * * *

UNITED STATES PATENT AND TRADEMARK OFFICE
CERTIFICATE OF CORRECTION

PATENT NO. : 4,749,742
DATED : June 7, 1988
INVENTOR(S) : Donald T. Elmore

It is certified that error appears in the above—identified patent and that said Letters Patent is hereby corrected as shown below:

Column 2, line 11 and Column 5, line 63, change the formula of the dialkyl phosphate ester to:

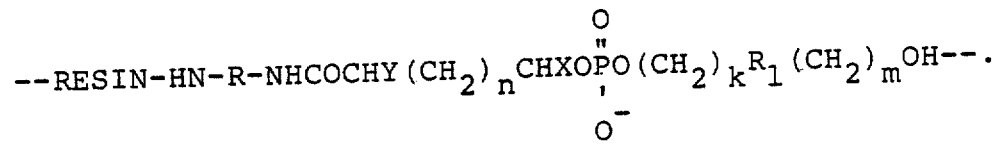

Column 5, line 55, delete "wherein l and m are integers from k to 4" and insert therefor --wherein k and m are integers from 1 to 4--.

Signed and Sealed this

Twenty-eighth Day of February, 1989

Attest:

DONALD J. QUIGG

Attesting Officer     Commissioner of Patents and Trademarks